Nov. 18, 1969 M. B. RUSSO ET AL Plant Pat. 2,940
PEACH TREE
Filed March 1, 1968
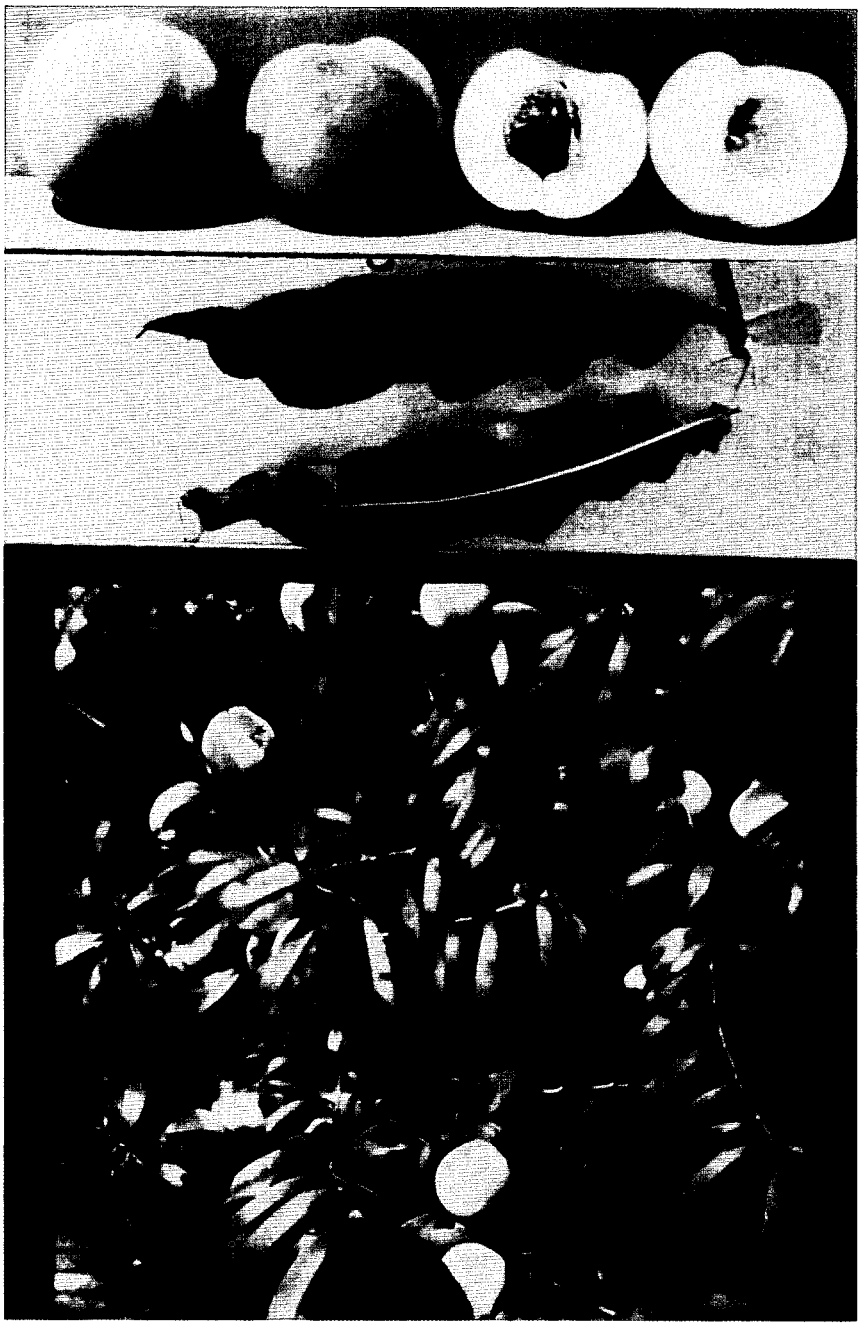
Inventors.
M. B. Russo
E. E. Slaybaugh
By: Robb & Robb
Attorneys.

United States Patent Office

Plant Pat. 2,940
Patented Nov. 18, 1969

2,940
PEACH TREE

Mariano B. Russo, Sewell, N.J., and Earl E. Slaybaugh, Towson, Md., assignors to Slaybaugh Bros. Nursery, Adams County, Pa., a partnership composed of Earl E. Slaybaugh and Raymond I. Slaybaugh

Filed Mar. 1, 1968, Ser. No. 709,843
Int. Cl. A01h *5/08*
U.S. Cl. Plt.—43 1 Claim

The present invention relates to a new and distinct variety of peach tree of the yellow-fleshed, freestone, fruit-bearing type, which was discovered by us, and which may be a whole tree sport of the peach variety known as "Rio Oso Gem" (Plant Patent No. 84).

At the time of our discovery, which occurred in an orchard mantained on cultivated property owned by Mariano B. Russo, near Sewell, in the county of Gloucester, and State of New Jersey, our attention was attracted, in the course of caring for and inspecting an orchard of "Rio Oso Gem" peach trees, to one particular tree on which the fruit ripened about ten days earlier than any of the adjacent "Rio Oso Gem" trees in the orchard. Steps were therefore jointly taken by us to carefully preserve the original tree, keep it under close observation, and to bud the same to other trees for test purposes, as performed by us at Aspers, Adams County, Pa. Continued observations of the original tree and the progeny thereof derived by budding, consistently confirmed the early ripening habit of the new variety, and the fact that this characteristic, along with others generally resembling those of the variety "Rio Oso Gem," but differing therefrom in some respects, represents a unique combination of characteristics which distinguish the same from "Rio Oso Gem" and from all other peach varieties of which we are aware, as evidenced by the following features which are outstanding in the new sport:

(1) A tree size and shape generally similar to "Rio Oso Gem," but sometimes a little larger in size;

(2) A more vigorous tree habit, but with tough branches that are not brittle;

(3) Non-showy blooms instead of the typical large and showy blooms of "Rio Oso Gem";

(4) Smaller fruit buds than those of "Rio Oso Gem";

(5) A general resemblance of the fruit to that of "Rio Oso Gem," but being slightly larger in size and having a more attractive color and appearance, with a smoother suture;

(6) An earlier fruit ripening habit, averaging about ten days earlier than the fruit of "Rio Oso Gem"; and (7) Good resistance to canker and brown rot.

The accompanying drawing shows typical specimens of the fruit and foliage of our new variety, with the fruit being illustrated in both elevation and in longitudinal cross-section, and with the leaf specimens illustrating both the upper and under surfaces thereof, all as depicted in color as nearly true as it is reasonably possible to make the same in a color illustration of this character.

The following is a detailed description of our new peach variety, with color terminology in accordance with Maerz and Paul Dictionary of Color (hereinafter abbreviated as (M & P)), or Nickerson's Color Fan (hereinafter abbreviated as (N)), as indicated, except where general color terms of ordinary dictionary significance are obvious:

Parentage: Believed to be a whole tree sport of "Rio Oso Gem."

Locality where grown and observed: Near Sewell, Gloucester County, N.J.

Dates of first and last pickings: About Aug. 23 and Aug. 28, respectively.

Tree: Medium size; vigorous; spreading; open; hardy (produces regular crops when spring frosts or cold temperatures reduces crops of "Rio Oso Gem" to less than 25% in the same area); very productive; regular bearer.

*Trunk.*—Medium stockiness; medium shagginess, but tending toward a shaggy form.

*Branches.*—Medium caliper; medium shagginess; dull.

*Color.*—Mauve Taupe Copra, Plate 7–C–8, page 37 (M&P).

*Lenticels.*—Medium number; large size.

*Leaves.*—Medium size; lanceolate; medium thickness; smooth.

*Length.*—About 5 inches.

*Width.*—About 1¼ inches.

*Color.*—Strong Green, Hue 5 G 4/7 (N).

*Margin.*—Finely serrate.

*Petiole.*—Medium length; medium thickness.

*Glands.*—None observed.

*Stipules.*—None.

Flower buds: Hardy; medium size; medium length; slightly pointed; appressed; pubescent; dormant buds not exposed as is the case in "Rio Oso Gem."

Flowers:

*Dates of first and full bloom.*—Usually 2 or 3 days after "Rio Oso Gem," but ranges from about Mar. 15 to about Apr. 5, with from about 3 to 5 days between first and full bloom, depending on weather conditions; medium early in comparison with other varieties.

*Size.*—Small (about one-half the size of the flowers of "Rio Oso Gem"); non showy.

*Color.*—Light Yellowish Pink, Hue 2.5 YR 9/3 (N).

Fruit:

*Maturity when described.*—Hard under-ripe (10 days before "Rio Oso Gem").

*Size.*—Uniform.

*Axial diameter.*—About 2½ inches.

*Transverse diameter in suture plane.*—About 2½ inches.

*Diameter at right angles to suture plane.*—About 2½ inches.

*Form.*—Uniform unsymmetrical; globose.

*Suture.*—Distinct; medium depth; extends from base to beyond, but discontinuous at apex; has slight depression beyond pistil point.

*Ventral surface.*—Lipped, with lips equal.

*Cavity.*—Flaring; elongated in suture plane, with suture showing on one side.

*Depth.*—About ⅜ inch.

*Breadth.*—About ¾ inch.

*Markings.*—Similar to "Rio Oso Gem."

*Base.*—Oblique.

*Apex.*—Short; oblique pistil point.

*Stem.*—Stout; glabrous; medium adherence to stone.

*Length.*—About ½ inch.

*Skin.*—Medium thickness; medium tenderness; tenacious to flesh, but free if over-ripe; no tendency to crack in wet or dry seasons.

*Color.*—Vivid Red, Hue 5 R 5/13 (N).

*Down.*—Scant; short; does not roll up when rubbed.

*Flesh.—Color.*—Moderate Orange Yellow, Hue 10 YR 8/10 (N).

*Surface of pit cavity.—Color.*—Red, with yellow fibres.

*Amygaldin.*—Moderate.

*Juice.*—Moderate quantity.

*Texture.*—Firm; fine; meaty; melting.

*Fibres.*—Few; fine; tender.

*Ripens.*—Evenly on both lips.

*Flavor.*—Mild; better than "Rio Oso Gem."

*Aroma.*—Pronounced.

*Eating quality.*—Good.

Stone: Free; parts from flesh smoothly.

*Size.*—Medium.

*Length.*—About 1½ inches.

*Breadth.*—About 1⅛ inches.

*Thickness.*—About ¾ inch.

*Form.*—Obovoid; cuneate toward base.

*Base.*—Oblique.

*Hilum.*—Narrow.

*Apex.*—Acute.

*Sides.*—Equal.

*Surface.*—Irregularly furrowed throughout; ridged throughout.

*Ridges.*—Rounded.

*Pits.*—Angular.

*Ventral edge.*—Thick; without wing throughout.

*Dorsal edge.*—Shallow grooves throughout; ridges on either side interrupted.

*Color.*—Strong Red, Hue 5 R 4/12 (N).

*Tendency to split.*—Has never shown any splitting in wet or dry seasons.

Disease resistance: No indications of canker and no susceptibility to brown rot, as determined by comparison with other varieties grown under the same conditions near Sewell, N.J., and when adjacent trees of "Rio Oso Gem" clearly showed the presence of canker.

Use: Dessert; culinary; canning.

Keeping quality: Good.

Shipping quality: Good.

We claim:

A new and distinct variety of peach tree of the yellow-fleshed, freestone, fruit-bearing type, substantially as herein shown and described, characterized particularly as to novelty by the unique combination of a tree size and shape generally similar to "Rio Oso Gem," but sometimes a little larger in size, a more vigorous tree habit, but with tough branches that are not brittle, non-showy blooms instead of the typical large and showy blooms of "Rio Oso Gem," smaller fruit buds than those of "Rio Oso Gem," a general resemblance of the fruit to that of "Rio Oso Gem," but being slightly larger in size and having a more attractive color and appearance, with a smoother suture, an earlier fruit ripening habit, averaging about ten days earlier than the fruit of "Rio Oso Gem," and good resistance to canker and brown rot.

No references cited.

ROBERT E. BAGWILL, Primary Examiner